United States Patent
Solanky et al.

(10) Patent No.: US 7,211,675 B2
(45) Date of Patent: May 1, 2007

(54) ANTIOZONANT BASED ON FUNCTIONALIZED BENZOTRIAZOLE UV ABSORBERS AND THE PROCESS THEREOF

(75) Inventors: Shailendra Singh Solanky, Pune (IN); Shrojal Mohitkumar Desai, Pune (IN); Raj Pal Singh, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 257 days.

(21) Appl. No.: 10/804,884

(22) Filed: Mar. 19, 2004

(65) Prior Publication Data
US 2005/0143584 A1 Jun. 30, 2005

Related U.S. Application Data

(63) Continuation of application No. PCT/IB2003/006204, filed on Dec. 25, 2003.

(51) Int. Cl.
C07D 249/16 (2006.01)
C07D 403/00 (2006.01)

(52) U.S. Cl. .................................. 548/257
(58) Field of Classification Search ........... 548/257
See application file for complete search history.

(56) References Cited

U.S. PATENT DOCUMENTS

| | | | |
|---|---|---|---|
| 3,409,586 A | 11/1968 | Oberster | 260/45.9 |
| 3,424,713 A | 1/1969 | Oberster et al. | 260/45.9 |
| 3,542,691 A | 11/1970 | Budd et al. | 252/401 |
| 3,663,505 A | 5/1972 | Hoffman | 260/45.9 |
| 3,839,275 A | 10/1974 | Wilder | 260/45.9 |
| 4,520,171 A | 5/1985 | Diveley William R. | 525/279 |
| 4,709,041 A | 11/1987 | Mehta | 548/260 |
| 4,857,596 A | 8/1989 | MacLeay et al. | 525/142 |
| 5,420,204 A | 5/1995 | Valet et al. | 525/125 |
| 5,569,716 A | 10/1996 | Okamoto et al. | 525/192 |
| 5,593,701 A | 1/1997 | Graves et al. | 425/52 |
| 5,721,298 A | 2/1998 | Waterman | 524/100 |
| 5,807,963 A | 9/1998 | Rosenquist | 528/196 |
| 5,834,544 A | 11/1998 | Lin et al. | 524/217 |
| 5,929,166 A | 7/1999 | Bomal et al. | 525/102 |
| 5,965,641 A | 10/1999 | Gugumus | 524/86 |
| 5,990,310 A | 11/1999 | Barrows | 544/197 |
| 5,997,769 A | 12/1999 | Tittmann et al. | 252/403 |
| 6,046,263 A | 4/2000 | Rasberger et al. | 524/284 |
| 6,284,895 B1 * | 9/2001 | Thanki et al. | 548/260 |
| 6,297,378 B1 | 10/2001 | Gupta et al. | 544/216 |
| 6,306,939 B1 | 10/2001 | Gupta et al. | 524/100 |
| 6,320,056 B1 * | 11/2001 | Thanki et al. | 548/259 |
| 6,329,473 B1 | 12/2001 | Marten et al. | 525/438 |
| 6,362,278 B1 | 3/2002 | Pfaendner et al. | 525/69 |
| 6,365,652 B2 | 4/2002 | Gupta et al. | 524/100 |
| 6,368,520 B1 | 4/2002 | Gugumus | 252/401 |
| 6,369,267 B1 | 4/2002 | Toan et al. | 560/144 |
| 6,448,208 B1 | 9/2002 | Dubs et al. | 508/229 |
| 6,492,518 B1 * | 12/2002 | Desai et al. | 546/14 |
| 6,492,521 B2 | 12/2002 | Sassi et al. | 546/188 |

FOREIGN PATENT DOCUMENTS

| | | |
|---|---|---|
| DE | 273644 | 11/1989 |
| GB | 1035262 | 7/1966 |

OTHER PUBLICATIONS

Konstantinova et al. (1994) "Synthesis and application of UV stabilizers for polymeric materials based on triazinylaminobenzotriazole", Degradation and Stability 43: 187-193.

Yoshida et al. (1982) "Synthesis and Polymerization of 2(2-Vinyl-4-hydroxyphenyl)2H-benzotriazole and 2(3-Vinyl-4-hydroxyphenyl)2H- benzotriazole", Monatshefte für Chemie 113: 603-622.

Yoshida et al. (1982) "Synthesis and Polymerization of 2(2-Hydroxy-5-Methylphenyl)-5Vinyl-2H-Benzotriazole", Journal of Polymer Science 20: 2215-2230.

(Continued)

*Primary Examiner*—Joseph K. McKane
*Assistant Examiner*—Susannah L. Chung
(74) *Attorney, Agent, or Firm*—Baker Botts L.L.P.

(57) ABSTRACT

A process for the preparation of a novel antiozonant and antioxidant, based on functionalized benzotriazole UV absorbers, and the process for the preparation thereof having a general Formula I:

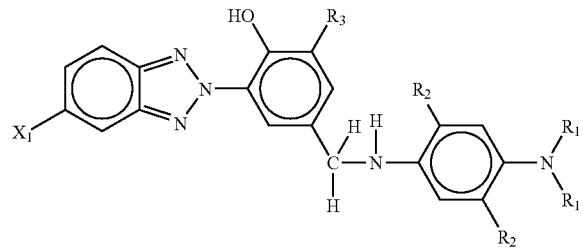

Formula I wherein $R_1$ and $R_2$ are $C_1$ to $C_8$ linear or branched alkyl; $R_3$ is hydrogen, tert-butyl; $X_1$ is select the group consisting of hydrogen, halogen, tert-butyl and $C_1$ to $C_{12}$ alkoxy.

7 Claims, No Drawings

OTHER PUBLICATIONS

Yoshida et al. (1982) "Synthesis and Polymerization of 2(2-Hydroxy-5-vinylphenyl)-2*H*-Benzotriazole", Makromol. Chem.., 183: 259-279.

Grillot et al. (1965) "The mechanism of the acid-catalyzed rearrangement of N-arylaminomethyl aryl sulfides", J. Org. Chem., 30: 28-33.

Lau et al. (1963) "Acid-catalyzed rearrangement of N-arylaminomethyl aryl sulfides", J. Org. Chem., 28: 2763-2765.

Grillot et al. (1959) "Condensation of thiophenols and formaldehyde with some aromatic amines", The Journal of Organic Chemistry 24: 1035-1038.

* cited by examiner

ANTIOZONANT BASED ON FUNCTIONALIZED BENZOTRIAZOLE UV ABSORBERS AND THE PROCESS THEREOF

CROSS-REFERENCE TO RELATED APPLICATIONS

This is a continuation of International Application No. PCT/IB2003/006204, filed Dec. 25, 2003, which is incorporated by reference herein in its entirety.

FIELD OF THE PRESENT INVENTION

This invention relates to the preparation of a novel antiozonant and antioxidant, based on functionalized benzotriazole UV absorbers, and the process for the preparation thereof, which can be used as a prerequisite of a polymer stabilizer and with other polymer stabilizers.

BACKGROUND OF THE INVENTION

N-alkyl, N'-phenyl-p-phenylene diamines are disclosed in U.S. Pat. Nos. 5,929,166; 5,593,701; 6,329,473; 3,409,586; 3,424,713; 3,542,691; 3,663,505; 3,839,275 and British Patent No. 1,035,262. Sulphur containing para-phenylene diamines are disclosed in U.S. Pat. No. 3,035,014.

A one step acid catalyzed reaction with thiols, formaldehyde and aromatic amines is known in the prior art (J. Org. Chem., 24, 1035 (1959); J. Org. Chem., 28, 2763 (1963) and J. Org. Chem., 30, 28 (1965). Side chain bromination in UV absorbers are disclosed in the literature (S. Yoshida & O. Vogl, Makromol. Chem., 183, 259 (1982); S. Yoshida, C. P. Lillya & O. VogI, Monatshefte Chem., 113, 603 (1982); S. Yoshida, C. P. Lillya & O. Vogl, J. Polym. Sci., Polym. Chem. Ed., 20, 2215 (1982); U.S. Pat. Nos. 6,284,895 and 6,320,056 of P. N. Thanki & R. P. Singh).

As known to those skilled in the art, degradation of rubber from ozone manifests itself by the appearance of (i) cracks perpendicular to the stress in the rubber and (ii) a silvery film on the surface of the article. The attack of ozone is a purely surface phenomenon. The function of the antiozonant depends on its migration to the surface of the rubber article.

Conventional diphenyl diamine antiozonants are widely used in the protection of rubber. Whereas these diphenyl diamines have in the past proved quiet satisfactory, recent developments in rubber technology have resulted in rubber products with extended service life and, therefore, require commensurate protection from ozonolysis. Therefore, there exists a need of new and efficient antiozonants offering extended protection from ozone. The present invention relates to polymeric antiozonants and their use in diene containing polymers.

Amine containing antiozonants are commonly used in diene rubbers to avoid degradation through ozonolysis and oxidation. Common examples of such anti oxidants are N,N-di-substituted p-phenylene diamines. There is a continuing need of superior anti ozonants to further prolong the useful life of these rubber products. The present invention relates to a composition comprising a high molecular weight amine-containing antiozonant that is prepared in a two-step process.

Most thermoplastic polymers and coating compositions are unstable to extended exposure to an ultraviolet light source in atmosphere. Thermoplastics and coatings tend to demonstrate unwanted color changes and reduced mechanical strength upon exposure to UV and thermal radiation. The preliminary effect of ultraviolet radiation on polymers is the formation of free radicals on the polymer chain, which react with atmospheric oxygen. This results in the formation of peroxide groups. Furthermore, decomposition of peroxide groups causes formation of carbonyl groups and chain scission. Irradiation in absence of oxygen causes the increase in crosslinking. Ultimately, this reflects on the mechanical properties and the color of the polymeric materials. In order to prevent or at least retard the damage caused by these factors, stabilizers are added to the plastics.

Antioxidants are tcompounds which, upon addition to the polymers, are capable of preventing or retarding the reactions of degradation caused by heat and light energy in the presence of oxygen. Triazines are one of the most important antioxidants, which are used commercially. There are many patents about the preparation and use of functional antioxidant in polymers and coatings.

Monomeric and low molecular weight antioxidants have limited use due to their properties of migration and leaching. This phenomenon could lead to uneven distribution of antioxidants within the polymeric matrix. Leaching could be even more harmful as the loss of antioxidants from the polymer matrix could lead to extensive thermal and photodegradation of the substrate. Therefore, in order to prevent the phenomena of migration and leaching, antioxidants with polymerizing ability are being developed. This particular class of stabilizers would have even distribution within the polymer matrix and also they overcome the phenomena of migration and leaching.

U.S. Pat. No. 4,520,171 (Diveley William R. et al.) relates to a new class of polymeric hindered amine light stabilizers based on maleic anhydride modified polyolefins reacted with tetramethyl piperidine derivatives. These materials are more effective than most of the generally used hindered amine light stabilizers. Due to their higher molecular weights and the polyolefin backbone, they are more compatible with polyolefins.

U.S. Pat. No. 4,709,041 (Mehta) discloses 2-(formylphenyl)benzotriazole intermediates that are versatile intermediates, which can be derivatized by reaction of the formyl group to provide a wide variety of ultraviolet-absorbing substituted 2-(2-hydroxyphenyl)-2H-benzotriazoles.

U.S. Pat. No. 4,857,596 (MacLeay et al.) discloses polymer bound antioxidants having antioxidant stabilizer groups chemically bound to polymers or copolymers by an acylaminoimide or diacylhydrazide function. The polymer bound antioxidants are prepared by reacting hydrazido substituted antioxidants with some or all of the anhydride groups of anhydride containing polymers or copolymers. The concentration of the stabilizers bound to the polymer may be readily varied depending upon the application of the polymer. Polymer with high concentrations of bound antioxidants can be used as masterbatches to stabilize other polymer systems.

U.S. Pat. No. 5,420,204 (Valet et al.) discloses light-stabilized copolymer compositions as paint binders. Curable compositions comprising (a) a fluorine- or silicon-containing copolymer, (b) a (meth)acrylic copolymer and (c) at least one curing agent are described, each of the two copolymers comprising functional groups which can react with the curing agent, wherein the fluorine- or silicon-containing copolymer comprises a UV absorber which is chemically bound by reaction with the free reactive groups of the copolymer. These copolymer compositions can be used as paint binders.

U.S. Pat. No. 5,569,716 (Okamoto et al.) discloses a rubber composition composed of (a) a hydrocarbon rubber, (b) a vulcanizing agent and/or crosslinking agent, and (c) a hydrogenated petroleum resin having a bromine number not greater than 10 (g/100 g). The rubber composition exhibits improved process ability over hydrocarbon rubber used alone but has no bad influence on the physical properties and heat resistance of its vulcanization. It is free from any trouble involved in crosslinking with a peroxide which is often used for EPR and EPDM. Therefore, it will find general use in the rubber industry.

U.S. Pat. No. 5,807,963 (Rosenquist Niles R.) discloses the synthesis of high molecular weight stabilizer compounds for stabilizing polymers. A high molecular weight stabilizer compound formed as an ester of 3-(2H-benzotriazol-2-yl)-5-(1,1-dimethylethyl)-4-hydroxy-benzene-propanoic acid or structural variants thereof, to impart improved resistance to the effects of ultraviolet radiation to polycarbonate comprising polymers, a process for the preparation of said compound, and articles of manufacture comprising said compound.

U.S. Pat. No. 5,721,298 (Waterman Paul Sheldon) discloses polymers stabilized against degradation by the addition of a liquid composition comprising an organic solvent and at least 40% by weight of triazine UV absorbers.

U.S. Pat. No. 5,834,544 (Lin Chung-Yuan et al.) discloses organic materials stabilized by compounds containing both amine and hindered phenol functional functionalities. The invention relates to compounds containing dual substitutions of an aromatic amine and hindered phenol functionality useful as stabilizers for organic materials.

U.S. Pat. No. 5,997,769 (Tittmann Rolf) discloses novel stabilizer mixtures suitable for stabilizing organic material, especially textile fiber materials, against damage by light, oxygen and heat.

U.S. Pat. No. 5,965,641 (Gugumus) discloses the synthesis of ozone-resistant long-term stabilizers. The invention relates to a process to stabilize an organic polymer against ozone in the ambient air, which comprises adding to the polymer as stabilizer, a monomeric sterically hindered piperidine compound or an oligomeric or polymeric sterically hindered piperidine compound containing one or several triazine units or a secondary sterically hindered piperidine compound.

U.S. Pat. No. 5,990,310 (Barrows Franklin H. A) discloses a method for the preparation of substituted triazines includes reacting a phenylazoaniline with a cyanuric halide to produce a (phenylazo)phenylamino-1,3,5-triazine followed by reduction to form an aminoanilino-1,3,5-triazine. The aminoanilino-1,3,5-triazine can be alkylated under reducing conditions to produce an N-alkyl-phenylenediamino-1,3,5-triazine such as 2,4,5-tris-[N-alkyl-p-phenylenediamino]-1,3,5-triazine, which is useful as an antiozonant in rubber and other polymer formulations.

U.S. Pat. No. 6,046,263 (Rasberger Michael) discloses the use of liquid antioxidants as stabilizers. The described compositions can be used as liquid antioxidants in organic materials.

U.S. Pat. No. 6,284,895 (Thanki, et al.) discloses the use of bromo-functionalized benzotriazole UV absorbers.

U.S. Pat. No. 6,306,939 (Gupta Ram Baboo et al.) discloses a novel carbamate containing trisaryl-1,3,5-triazines and the use thereof as an ultraviolet light absorber. In particular, the presently claimed compounds comprise a carbamate triazine polymer, which either alone or in combination with other additives, including other ultraviolet light absorbers and stabilizers, can be used in stabilizing a polymeric film or molded article from degradation due to exposure to actinic radiation.

U.S. Pat. No. 6,297,378 (Gupta Ram B. et al.) discloses a novel process for making 2-(2-hydroxy-4-alkoxyphenyl)-4,6-bisaryl-1,3,5-triazine and 2-(2,4-dialkoxyphenyl)-4,6-bisaryl-1,3,5-triazine compounds directly from 2-chloro-4,6-bisaryl-1,3,5-triazine compounds with 3-alkoxyphenol, 1,3-dialkoxylbenzene compounds or mixtures thereof.

U.S. Pat. No. 6,492,521 (Sassi Thomas P.) discloses hindered amine light stabilizers based on multi-functional carbonyl compounds and methods of making same.

U.S. Pat. No. 6,362,278 (Pfaendner, Rudolf et al.) discloses a process for stabilizing and concurrently compatibilizing plastics or plastic compositions by incorporating polymeric compounds obtained by reacting a compound selected from the group consisting of the sterically hindered phenols, sterically hindered amines, lactones, sulfides, phosphites, benzotriazoles, benzophenones and 2-(2-hydroxyphenyl)-1,3,5-triazines, which are compounds containing at least one reactive group, with a compatibilizator.

U.S. Pat. No. 6,448,208 (Dubs, Paul et al.) discloses the synthesis of liquid polyfunctional additives.

U.S. Pat. No. 6,369,267 (Toan, Vien Van et al.) discloses the synthesis of polyoxyalkylene substituted, bridged triazine, benzotriazole and benzophenone derivatives as UV absorbers. Triazine, benzotriazole and benzophenone derivatives, which are substituted or bridged with polyoxyalkylene groups, and their use as UV absorbers in photographic materials, such as inkjet inks and printing inks, transfer prints, paints and varnishes, organic polymeric materials, plastics, rubber, glass, packaging materials, sunscreens of cosmetic preparations and skin protection compositions, are disclosed.

U.S. Pat. No. 6,368,520 (Gugumus) discloses a synergistic stabilizer mixture.

U.S. Pat. No. 6,365,652 (Gupta Ram Baboo et al.) discloses an amido or carbamate substituted trisaryl-1,3,5-triazines and the use thereof to protect against degradation by environmental forces, inclusive of ultraviolet light, actinic radiation, oxidation, moisture, atmospheric pollutants and combinations thereof. The new class of trisaryl-1,3,5-triazines comprises an aryl ring attached to the triazine ring substituted with a group comprising a bondable amido/carbamate containing group para- to the point of attachment to the triazine ring. These materials may, under the appropriate circumstances, be bonded to formulations comprising coatings, polymers, resins, organic compounds and the like via reaction of the bondable functionality with the materials of the formulation. A method for stabilizing a material by incorporating such amido or carbamate substituted trisaryl-1,3,5-triazines is also disclosed.

U.S. Pat. No. 6,492,518 (Desai S. M. et al.) relates to Tinuvin P-hindred amine light stabilizer and derivatives thereof.

Buechner et al. (DD 273644 A1 22 Nov. 1989, 4 pp) discloses multivalent lubricant additives on the basis of aminomethylated benzotriazole derivatives, prepared by diazotization of o-phenylenediamine and subsequent aminomethylation of the resulting reaction products containing organic and inorganic transition-, by- and intermediate-products in the reaction medium.

Konstantinova, A. et al. ("Synthesis and application of UV stabilizers for polymeric materials based on triaziny-laminobenzotriazole" Polym. Degrad. Stab., 43, 187 (1994)) discloses the synthesis of four derivatives of triazinylaminobenzotriazole, containing a polymerizable allyloxy group. The compounds were characterized by elemental analysis, TLC, IR, UV and $^1$H NMR spectra. The spectral (absorption and fluorescence) characteristics of the compounds have been investigated, showing that 45–85% of the compounds are bound. Maximum stabilizing effect is achieved with 1 wt % initial concentration of the stabilizer.

The main objective of the present invention to provide a process for the preparation of novel derivatives of a combination of antioxidant and antiozonant, which can fulfill the prerequisites of a polymer stabilizer and can be used with other polymer stabilizers.

Another object of present invention is the preparation of compounds having antioxidant as well as antiozonant properties.

Yet another object of present application is to generate an economic, as well as high yielding, process of preparation of derivatives with antiozonant properties.

Moreover, this class of combination of benzotriazoles and diamines is known to be compatible with polyolefins, polycarbonate, polystyrene and diene-elastomers and can even be added in an additive proportion to obtain desired thermal stability of various other polymers.

SUMMARY OF THE PRESENT INVENTION

The present invention relates to N,N-di substituted paraphenylene diamines which offer protection to polymers, such as natural rubber against the deteriorous effects of oxygen and ozone. It also relates to methods for preparation and use of these materials and compositions formed by mixing these materials with polymers. Para-phenylene diamines have been used as antioxidants and antiozonants.

DETAILED DESCRIPTION OF PRESENT INVENTION

Accordingly, the present invention provides a functionalized benzotriazole compound having general Formula I

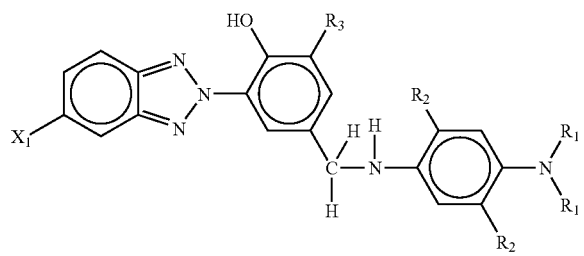

Formula I wherein $R_1$ and $R_2$ are $C_1$ to $C_8$ linear or branched alkyl; $R_3$ is hydrogen, tert-butyl; $X_1$ is select the group consisting of hydrogen, halogen, tert-butyl and $C_1$ to $C_{12}$ alkoxy, where the compound has antioxidant and antiozonant properties, and a process for the synthesis thereof.

The present invention also provides a process for the preparation of novel antiozonant based on functionalized benzotriazole UV absorbers comprising (a) dissolving a compound of Formula III

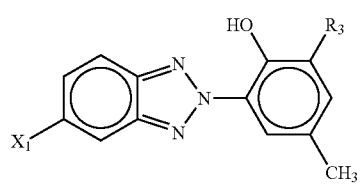

Formula III wherein $R_3$ is hydrogen, tert-butyl and $X_1$ is selected the group consisting of hydrogen, halogen, tert-butyl and $C_1$ to $C_{12}$ alkoxy with bromine in a non polar organic solvent at a temperature range 45 to 85° C. for a period of 4 to 9 hours, (b) evaporating the solvent under reduced pressure to obtain a compound having general

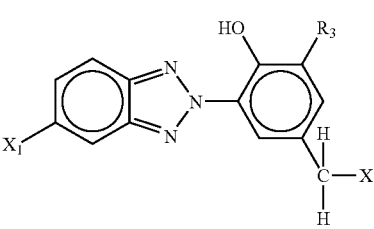

Formula II

Formula II wherein, $R_3$ is hydrogen, tert-butyl, $X_1$ is selected the group consisting of hydrogen, halogen, tert-butyl and $C_1$ to $C_{12}$ alkoxy and X is Br, (c) treating the compound of general Formula II with compound having general Formula IV

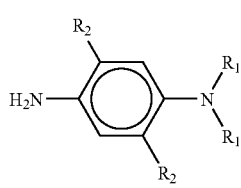

Formula IV wherein $R_1$ and $R_2$ are $C_1$ to $C_8$ linear or branched alkyl in presence of an organic solvent using a mild base at a temperature of 45–80° C. for a period of 4 to 5 hours, (d) bringing the reaction mixture to room temperature, (e) separating the organic layer and (f) concentrating the product by solvent evaporation under reduced pressure and (g) purifying the final product of general Formula I by column chromatography.

In one embodiment of the present invention, the neutral organic solvent used for dissolving the compound having general Formula III is selected from the following chlorinated solvents: carbon tetrachloride, chloroform, chlorobenzene and dichloromethane.

In another embodiment of the present invention, the bromination of compound of general Formula III is achieved by using liquid bromine.

In still another embodiment, the para-phenylene diamine having general Formula IV is selected from N,N-dimethyl-para-phenylene diamine, N,N-diethyl-para-phenylene diamine, 2,5-dimethyl-para-phenylene diamine and 2,5-diethyl-para-phenylene diamine.

In still another embodiment, the solvent used to dissolve the para-phenylene diamine is acetone.

In still another embodiment, the mild inorganic base is selected from potassium carbonate, sodium carbonate, potassium bicarbonate and sodium bicarbonate.

The disclosure made herewith is the invention of a novel antioxidant coupled to an antiozonant and their derivatives. These classes of compounds are added to polymers in order to improve their thermal stability and improve their resistance towards oxidative degradation during their processing and service life. They can also be used in the formulation of photostable coatings and paints for outdoor applications. This class of stabilizers is found to be compatible with polyolefins, polycarbonate, and a variety of diene elastomers. This novel is expected to work in synergism with the UV absorbers and radical scavengers used as additives for polymer photo-stabilization. This antioxidant would also find potential applications in consumer care products, cosmetics and pharmaceuticals.

The process disclosed by the present invention has four distinct merits:
1) The bromination of benzotriazole UV absorber does not involve use of any radical initiator or catalyst.
2) The process is economic and gives a high yield of product.
3) The process uses commonly available organic reagents and mild reaction conditions.
4) Reaction can be carried out via a very facile route with very simple and moderate reaction conditions.

EXAMPLE 1

This example describes the synthesis of 2-(2H-Benzotriazole-2-yl)-4-bromomethylphenol/2-Benzotriazol-2-yl-4-bromomethyl-phenol. 2-(2H-Benzotriazole-2-yl)-4-bromomethylphenol was prepared from the bromination of 2-(2H-Benzotriazole-2-yl)-4-methylphenol. In a 250 ml three-necked round bottomed flask, 2-(2H-Benzotriazole-2-yl)-4-bromomethylphenol (4.0 g; 0.0112 mol) was dissolved in 30 ml of dry carbon tetrachloride. In a separate conical flask, bromine (0.748 ml; 0.01176 mole) was dissolved in 45 ml of dry carbon tetrachloride and solution was transferred to a cylindrical funnel with pressure equalizing tube. Three-necked round-bottom flask containing solution of 2-(2H-Benzotriazole-2-yl)-4-bromomethylphenol was kept in oil-bath at 45° C. for 4 hrs and followed by 85° C. for 9 hrs. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature. The product was separated by solvent evaporation. Finally the product obtained was fine white crystalline and was absolutely pure. The yield of 2-(2H-Benzotriazole-2-yl)-4-bromomethylphenol was 4.071 g (75%), m.p. 169–171° C.

EXAMPLE 2

This example describes the synthesis of 4-[(4-Amino-phenylamino)-methyl]-2-benzotriazol-2-yl-phenol. Para-phenylene diamine (p-PDA) (2.1 equivalent, 0.373 g, 0.00345 mole), potassium carbonate (2.2 equivalent, 0.50 g, 0.00361 mole) and 25 ml acetone were magnetically stirred in a 100 ml two-necked round-bottom flask. 2-Benzotriazol-2-yl-4-bromomethyl-phenol (1 equiv., 0.5 g, 0.00164 mole) was dissolved in 50 ml of acetone and solution was transferred to a cylindrical funnel with pressure equalizing tube. Two-necked round-bottomed flask containing solution of p-PDA was kept in oil-bath at 80° C. 2-Benzotriazol-2-yl-4-bromomethyl-phenol solution was added drop-wise, from funnel to the flask for a span of 4–5 hours till all the solution was poured out. After that heating was stopped and the final reaction mixture was allowed to cool at room temperature. The product was separated by column chromatography. The yield was 63%.

EXAMPLE 3

This example describes the synthesis of 2-benzotriazol-2-yl-4-[(4-dimethyl amino-phenylamino)-methyl]-phenol. N,N-dimethyl-para-phenylene diamine (2.1 equivalent, 0.469 g, 0.00345 mole), potassium carbonate (2.2 equivalent, 0.50 g, 0.00361 mole) and 25 ml acetone were magnetically stirred in a 100 ml two-necked round-bottom flask. 2-Benzotriazol-2-yl-4-bromomethyl-phenol (1 equiv., 0.5 g, 0.00164 mole) was dissolved in 50 ml of acetone and solution was transferred to a cylindrical funnel with pressure equalizing tube. Two-necked round-bottomed flask containing solution of N,N-dimethyl-para-phenylene diamine was kept in oil-bath at 80° C. 2-Benzotriazol-2-yl-4-bromomethyl-phenol solution was added drop-wise, from funnel to the flask for a span of 4–5 hours till all the solution was poured out. After that heating was stopped and the final reaction mixture was allowed to cool at room temperature. The product was separated by column chromatography. The yield was 61%.

EXAMPLE 4

This example describes the synthesis of 4-[(4-Amino-2,5-dimethyl-phenylamino)-methyl]-2-benzotriazol-2-yl-phenol. 2,5-dimethyl-para-phenylene diamine (2.1 equivalent, 0.469 g, 0.00345 mole), potassium carbonate (2.2 equivalent, 0.50 g, 0.60361 mole) and 25 ml acetone were magnetically stirred in a 100 ml two-necked round-bottom flask. 2-Benzotriazol-2-yl-4-bromomethyl-phenol (1 equiv., 0.5 g, 0.00164 mole) was dissolved in 50 ml of acetone and solution was transferred to a cylindrical funnel with pressure equalizing tube. Two-necked round-bottomed flask containing solution of 2,5-dimethyl-para-phenylene diamine was kept in oil-bath at 80° C. 2-Benzotriazol-2-yl-4-bromomethyl-phenol solution was added drop-wise, from funnel to the flask for a span of 4–5 hours till all the solution was poured out. After that heating was stopped and the final reaction mixture was allowed to cool at room temperature. The product was separated by column chromatography. The yield was 52%.

EXAMPLE 5

This example describes the synthesis of 2-benzotriazol-2-yl-4-{[4-(1,3-dimethyl-butylamino)-phenylamino]-methyl}-phenol. N-(1,3-dimethyl-butyl)-benzene-1,4-diamine (2.1 equivalent, 0.621 g, 0.00345 mole), potassium carbonate (2.2 equivalent, 0.50 g, 0.00361 mole) and 25 ml acetone were magnetically stirred in a 100 ml two-necked round-bottom flask. 2-Benzotriazol-2-yl-4-bromomethyl-phenol (1 equiv., 0.5 g, 0.00164 mole) was dissolved in 50 ml of acetone and solution was transferred to a cylindrical funnel with pressure equalizing tube. Two-necked round-bottomed flask containing solution of N-(1,3-dimethyl-butyl)-benzene-1,4-diamine was kept in oil-bath at 80° C. 2-Benzotriazol-2-yl-4-bromomethyl-phenol solution was added dropwise, from funnel to the flask for a span of 4–5 hours till all the solution was poured out. After that heating was stopped and the final reaction mixture was allowed to cool at room temperature. The product was separated by column chromatography. The yield was 59%.

EXAMPLE 6

This example describes the synthesis of 2-benzotriazol-2-yl-4-[(4-phenylamino-phenylamino)-methyl]-phenol.
N-Phenyl-para phenylene diamine (2.1 equivalent, 0.6348 g, 0.00345 mole), potassium carbonate (2.2 equivalent, 0.50 g, 0.00361 mole) and 25 ml acetone were magnetically stirred in a 100 ml two-necked round-bottom flask. 2-Benzotriazol-2-yl-4-bromomethyl-phenol (1 equiv., 0.5 g, 0.00164 mole) was dissolved in 50 ml of acetone and solution was transferred to a cylindrical funnel with pressure equalizing tube. Two-necked round-bottomed flask containing solution of N-Phenyl-para phenylene diamine was kept in oil-bath at 80° C. 2-Benzotriazol-2-yl-4-bromomethyl-phenol solution was added drop-wise, from funnel to the flask for a span of 4–5 hours till all the solution was poured out. After that heating was stopped and the final reaction mixture was allowed to cool at room temperature. The product was separated by column chromatography. The yield was 67%.

EXAMPLE 7

This example describes the synthesis of 2-benzotriazol-2-yl-4-[(4-isopropyl amino-phenylamino)-methyl]-phenol.
N-isopropyl-para phenylene diamine (2.1 equivalent, 0.517 g, 0.00345 mole), potassium carbonate (2.2 equivalent, 0.50 g, 0.00361 mole) and 25 ml acetone were magnetically stirred in a 100 ml two-necked round-bottom flask. 2-Benzotriazol-2-yl-4-bromomethyl-phenol (1 equiv., 0.5 g, 0.00164 mole) was dissolved in 50 ml of acetone and solution was transferred to a cylindrical funnel with pressure equalizing tube. Two-necked round-bottomed flask containing solution of N-isopropyl-para phenylene diamine was kept in oil-bath at 80° C. 2-Benzotriazol-2-yl-4~bromomethyl-phenol solution was added drop-wise, from funnel to the flask for a span of 4–5 hours till all the solution was poured out. After that heating was stopped and the final reaction mixture was allowed to cool at room temperature. The product was separated by column chromatography. The yield was 54%.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. Various references are cited herein, the disclosure of which are incorporated by reference in their entireties.

We claim:

1. A functionalized benzotriazole compound of general Formula I

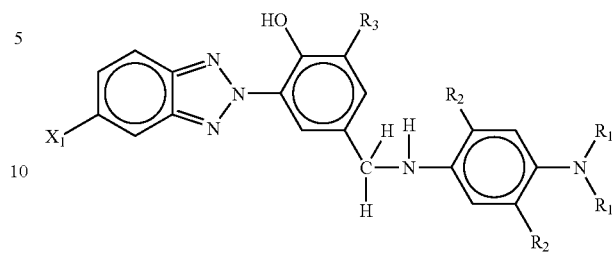

Formula I wherein $R_1$ and $R_2$ are selected from the group consisting of $C_1$ to $C_8$ linear and branched alkyls, $R_3$ is selected from the group consisting of hydrogen and tert-butyl, and $X_1$ is selected from the group consisting of hydrogen, halogen, tert-butyl and $C_1$ to $C_{12}$ alkoxy; and wherein the compound has antioxidant and antiozonant properties.

2. A process for preparing a functionalized benzotriazole having general Formula I comprising

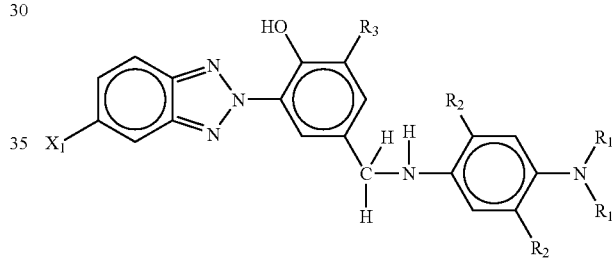

Formula I (a) dissolving a compound of general Formula III with bromine in a nonpolar organic solvent at a temperature between 45 to 85° C. for a period of 4 to 9 hours,

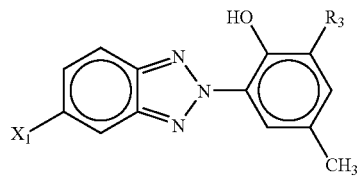

Formula III wherein $R_3$ is selected from the group consisting of hydrogen and tert-butyl, $X_1$ is selected from the group consisting of hydrogen, halogen, tert-butyl and $C_1$ to $C_{12}$ alkoxy;

(b) evaporating the nonpolar solvent under reduced pressure to obtain a compound having general Formula II,

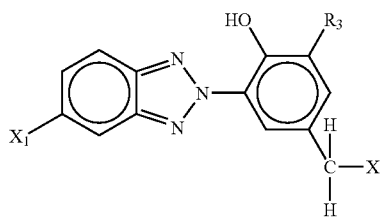

Formula II wherein
  $R_3$ is selected from the group consisting of hydrogen and tert-butyl,
  $X_1$ is selected from the group consisting hydrogen, halogen, tert-butyl and $C_1$ to $C_{12}$ alkoxy, and
  X is Br;
  (c) reacting the compound of general Formula II with a compound having a general Formula IV in the presence of an organic solvent and a mild base at a temperature of 45–85° C. for a period of 4 to 5 hours to produce a reaction mixture,

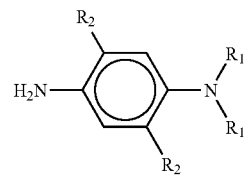

Formula IV wherein
  $R_1$ and $R_2$ are selected from the group consisting of $C_1$ to $C_8$ linear and branched alkyl;
  (d) bringing the reaction mixture to room temperature, wherein the reaction mixture has an organic layer containing the functionalized benzotriazole;
  (e) separating the organic layer;
  (f) concentrating the functionalized benzotriazole by solvent evaporation under reduced pressure; and
  (g) purifying the functionalized benzotriazole by column chromatography.

3. The process of claim 2, wherein the nonpolar organic solvent is a chlorinated solvent selected from the group consisting of carbon tetrachloride, chloroform, chlorobenzene and dichloromethane.

4. The process of claim 2, wherein the compound of Formula III is brominated with liquid bromine.

5. The process of claim 2, wherein the compound having general Formula IV is selected from the group consisting of N,N-dimethyl-para-phenylene diamine, N,N-diethyl-para-phenylene diamine, 2,5-dimethyl-para-phenylene diamine and 2,5-diethyl-para-phenylene diamine.

6. The process of claim 2, wherein the organic solvent for dissolving the compound having general Formula IV is acetone.

7. The process of claim 2, wherein the mild base is selected from the group consisting of potassium carbonate, sodium carbonate, potassium bicarbonate and sodium bicarbonate.

* * * * *